United States Patent [19]

Butte, Jr.

[11] 4,086,276

[45] Apr. 25, 1978

[54] ISOMERIZATION OF CYCLOHEXANEBIS(METHYLAMINE) STEREOISOMERS

[75] Inventor: Walter A. Butte, Jr., West Chester, Pa.

[73] Assignee: Suntech, Inc., Wayne, Pa.

[21] Appl. No.: 781,082

[22] Filed: Mar. 25, 1977

[51] Int. Cl.² .............................................. C07C 83/00
[52] U.S. Cl. ................................................. 260/563 R
[58] Field of Search .................................. 260/563 R

[56] References Cited

U.S. PATENT DOCUMENTS 3,344,164   9/1967   Seaton .............................. 260/563 X Primary Examiner—Paul F. Shaver
Attorney, Agent, or Firm—J. Edward Hess; Donald R. Johnson; Paul Lipsitz

[57] ABSTRACT

A process for isomerizing cyclohexanebis(methylamine) by contacting it with an organometallic compound at a temperature of from about 100° to about 200° C.

11 Claims, No Drawings

ISOMERIZATION OF CYCLOHEXANEBIS(METHYLAMINE) STEREOISOMERS

Disubstituted cyclohexane isomers exist in two isomeric forms, designated cis and trans according to the location of the substituents with respect to the cyclohexane ring. The isomeric composition often has important effects on the physical properties of products prepared from these cyclohexyl derivatives. For example, polyamides derived from isomer mixtures containing mostly trans-1,4-cyclohexanebis(methylamine) are generally much higher melting than the corresponding cis-polyamides. Therefore, it is desirable to have a means of adjusting the proportion of cis and trans forms in a mixture of such isomers.

It has been disclosed in the art that isomerization of 1,4-cyclohexane dicarbonitrile, 1,4-cyclohexanebis(methylamine) and 4-(aminomethyl)-cyclohexanemethanol can be carried out in the presence of a catalyst selected from the group consisting of lithium, sodium, potassium and their oxides, cyanides, amides, hydrides, hydroxides and borohydrides (U.S. Pat. No. 3,344,164). However, because the reaction rate is highly temperature dependent, these catalysts are preferably used at 200°–300° C and undesirable side reactions occur under these conditions which significantly reduces yields of desired products.

U.S. Pat. No. 3,829,490 discloses that the isomerization of $C_6$–$C_{14}$ cycloalkanebis(methylamine) compounds such as 1,4-cyclohexanebis(methylamine) can be carried out by contacting the isomer mixture at elevated temperature with hydrogen and ammonia in the presence of certain hydrogenation catalysts (e.g. Raney cobalt, palladium, platinum and ruthenium). A disadvantage of this process is the high pressure developed under the reaction conditions.

Also of interest in U.S. Pat. No. 3,251,874 which discloses the isomerization of a cis rich mixture of 1,4-cyclohexane dicarbonitrile to a mixture of about 42% cis and about 58% trans isomers by passing vapors of the isomer mixture together with ammonia over an alkaline earth metal oxide or activated alumina catalyst at elevated temperature.

An objective of this invention is to provide a more active catalyst that will permit the isomerization process to be carried out rapidly at relatively low temperature and at atmospheric pressure. A further objective is to obtain high yields of the isomerized product.

These objectives are accomplished by employing as catalyst an organometallic compound of an alkali metal at a temperature of from 100° to 200° C. In accord with the invention a process is provided for catalytically isomerizing a cyclohexane bis(methylamine) which comprises contacting said bis-amine with an alkali metal benzene compound at a temperature of from about 100° to about 200° C. Preferably, the alkali metal benzene compound will be prepared in situ from a phenylmethylamine and an alkali metal, an alkali metal amide or an alkali metal hydride. It is surprising that the alkali metal benzene compounds promote isomerization since it would be expected that elimination of ammonia would occur as predicted by currently accepted theories (C. Gould, Mechanism and Structure of Organic Chemistry, p. 478) rather than the reversible formation of a carbanionic intermediate which appears to be the isomerization mechanism.

In accordance with the invention, 1,2-, 1,3- or 1,4-cyclohexanebis(methylamine) can be isomerized very efficiently. In one embodiment the invention is used to adjust the proportion of cis and trans isomer content of an unequilibrated mixture of these isomers. In another embodiment it is applicable to the isomerization of pure cis or pure trans isomers.

The catalysts that are useful in the process are, as indicated, alkali metal benzene compounds and include the class of benzylic organoalkali compounds as disclosed by Coates, Green and Wade, Organometallic Compounds, 3rd ed., Vol. One, p. 49, Methuen & Co. Ltd. London (1967). Benzyl sodium, xylyl sodium, and benzyl potassium are typical members of this class of alkali metal benzene compounds.

Because of the high reactivity and poor thermal stability of benzylic organoalkali compounds, it is desirable to prepare the catalyst in situ by combining an alkali metal, alkali metal amide, or alkali metal hydride with a phenylmethylamine such as benzylamine, dibenzylamine or preferably xylylamine. The active organoalkali compound is formed very rapidly from these reagents as indicated by the development of intensely colored soluble species characteristic of benzylic organoalkali compounds. W. Krabbe et al., (Ber. 74 1343 (1941) describes this type of reaction for forming the organoalkali compound.

The process of the invention is carried out by combining the organometallic catalyst with the cyclohexanebis(methylamine) at reaction temperature and atmospheric pressure until the desired amount of isomerization has occurred. The rate of isomerization will depend upon the catalyst concentration and temperature. Satisfactory results are obtained at about 100°–200° C with 125°–175° C preferred. Below 100° C, the rate is impractically slow and above about 200° C, undesirable side reactions such as ammonia elimination become excessive.

While there is no fixed limit on the amount of catalyst, satisfactory results are obtained by using from 5 to 50 millimoles, based on the alkali metal, per mole of cyclohexanebis(methylamine). When the catalyst is prepared in situ, at least one millimole of phenylmethylamine is required to generate a millimole of catalyst, but larger quantities can be used as a means to replenish any catalyst that is destroyed by thermal decomposition during the process.

Since the catalyst is destroyed by oxygen, oxygenated solvents and water, the reactants should be inert to the catalyst complex and precautions should be taken to insure that air, moisture and other impurities are rigorously excluded. Although solvents are not needed, if a solvent is used it should be dry and free of air. Hydrocarbon solvents such as hexane and benzene are suitable.

The reaction time depends upon the temperature and catalyst level that is selected. Generally, contact times of less than six hours will provide the desired extent of reaction within the preferred temperature range and specified catalyst concentrations and, usually, less than 1 hour is adequate. It is undesirable to use contact times longer than necessary since side reactions may occur that will reduce the yield of isomerate.

The product is readily separated from the catalyst by distillation and it may be desirable to destroy the catalyst prior to distillation. This can be accomplished by adding stoichiometric amounts of air, water or hydroxylic solvent such as alcohol.

In order to further illustrate the invention, the following examples are given:

EXAMPLE 1

A slurry of 1.1 g. benzyl sodium in 3.4 g. heptane was added to 35 g. of 1,4-cyclohexanebis(methylamine) wherein the trans:cis isomer rate was 0.78. The deep red solution formed on mixing was heated to 100° C under nitrogen. After 2 hours, the amine was separated from the benzyl sodium by flash distillation at about 0.5 mm. Hg. Analysis showed that the recovered amine was 1,4-cyclohexanebis(methylamine) wherein the trans:cis isomer ratio was 1.5.

EXAMPLE 2

When the procedure of Example 1 was repeated except that the mixture was heated to 150° C, the trans:cis isomer ratio of the product was 2.8.

EXAMPLE 3

A suspension of 1.2 g. sodium in mineral oil (40%) was added to 30.9 g. 1,4-cyclohexanebis(methylamine) (0.65 trans:cis ratio). The mixture was heated to 150° C for 2.5 hours and then to about 240° C for 0.5 hours. Samples removed at each temperature were analyzed showing that no change in isomer composition had occurred.

The mixture was cooled at 30° C and 5 g. paraxylylamine was introduced. It was then heated to 150° C. A deep red color developed during heating. After one hour, the trans:cis ratio had increased to over 4.0.

EXAMPLE 4

A suspension of 0.3 g. sodium in mineral oil (40%) and 0.2 g. paraxylylamine was added to 5.0 g. 1,4-cyclohexanebis(methylamine) (0.65 trans:cis ratio) dissolved in 15 ml. decalin. The mixture was heated to about 190° C with development of red color. Samples were periodically removed for analysis. The trans:cis isomer ratio increased to 1.6 after 30 min., and to over 4.0 after 120 min. No further change occurred after 120 min. indicating that the isomers had reached equilibrium.

An identical experiment was carried out except that no para-xylylamine was added. After 5 hours, the trans:cis isomer ratio remained unchanged.

EXAMPLE 5

To a solution of 5.0 g. 1,4-cyclohexanebis(methylamine) in 15 ml. toluene, was added 0.3 g. sodium amide and 0.2 g. para-xylylamine. A soluble red species formed immediately. The solution was heated to 110° C and sampled periodically for analysis. From an initial 0.67, the trans:cis ratio increased to 1.8 after 2 hours and to 2.2 after 5 hours.

In an identical experiment except that no para-xylylamine was added, no isomerization occurred over the same period of time.

In another experiment that was otherwise identical, a catalyst of p-aminomethyl benzyl sodium was preformed by combining the sodium amide and para-xylylamine at reaction temperature for 0.5 hr. and then adding the 1,4-cyclohexanebis(methylamine). Samples removed for analysis showed that the trans:cis ratio has increased to 1.4 and 3.4 after two and six hours, respectively.

EXAMPLE 6

Various organo-nitrogen bases were evaluated as catalyst precursors in place of para-xylylamine according to the procedure of Example 5. The results, tabulated below, show that other compounds selected from the class of phenylmethylamines readily form active catalyst but that aliphatic amines and nitogen heterocycles such as n-butylamine and pyridine do not.

| Nitrogen Base | trans:cis ratio | |
|---|---|---|
| | inital | final |
| Para-xylylenediamine | 0.5 | 1.0 |
| Dibenzylamine | 0.5 | 1.0 |
| Benzylamine | 0.7 | 1.0 |
| n-Butylamine | 0.7 | 0.7 |
| Pyridine | 0.7 | 0.7 |

EXAMPLE 7

A mixture of 28.0 g. 1,4-cyclohexanebis(methylamine) (46% trans, 54% cis), 1.5 g. para-xylylamine and 150 mg. sodium amide was heated to 150° C. A deep red color developed. The reaction mixture was kept at 150° C for 0.5 hr. It was then cooled to about 100° C and flash distilled at reduced pressure. A clear, colorless distillate weighing 27.0 g., was obtained that was essentially pure 1,4-cyclohexanebis(methylamine) with 75% trans content. A red oil remained in the distillation pot containing the catalyst residue, i.e., the reaction products of sodium amide and para-xylylamine.

EXAMPLE 8

Isomerization of 1,4-cyclohexanebis(methylamine) was carried out essentially in accord with the procedure of Example 7 except that lithium, sodium hydride and potassium hydride were used in place of sodium amide. The results are tabulated below:

| | wt., mg. | % trans isomer | |
|---|---|---|---|
| | | initial | final |
| sodium hydride | 70 | 47 | 75 |
| lithium | 330 | 42 | 69 |
| potassium hydride | 250 | 42 | 52 |

The invention claimed is:

1. A process for catalytically isomerizing a cyclohexane bis(methylamine) which comprises contacting said bis-amine with an alkali metal benzene compound at a temperature of from about 100° to about 200° C.
2. The process of claim 1 wherein the alkali metal benzene compound is prepared in situ from a phenylmethylamine and an alkali metal, an alkali metal amide or an alkali metal hydride.
3. The process of claim 2 wherein the bis(methylamine) is 1,4-cyclohexanebis(methylamine).
4. The process of claim 3 wherein the alkali metal benzene compound is a benzyl sodium.
5. The process of claim 4 wherein the alkali metal benzene compound is a xylyl sodium.
6. The process of claim 3 wherein the alkali metal benzene compound is p-aminomethylbenzyl sodium.
7. The process of claim 4 wherein the benzyl sodium is prepared by reaction of benzylamine and sodium, sodium hydride or sodium amide.
8. The process of claim 5 wherein the xylyl sodium is prepared from para-xylylamine and sodium, sodium hydride or sodium amide.
9. The process of claim 5 wherein the xylyl sodium is prepared from p-xylylenediamine and sodium, sodium hydride or sodium amide.
10. The process of claim 2 wherein the alkali metal compound is sodium amide.
11. The process of claim 2 wherein the alkali metal compound is sodium hydride.

* * * * *